United States Patent [19]

Wuchinich et al.

[11] 4,052,987
[45] Oct. 11, 1977

[54] AUTOMATIC ASPIRATION APPARATUS

[75] Inventors: David G. Wuchinich; Alan Broadwin, both of New York, N.Y.

[73] Assignee: Cavitron Corporation, New York, N.Y.

[21] Appl. No.: 672,813

[22] Filed: Apr. 1, 1976

[51] Int. Cl.² .............................................. A61M 1/00
[52] U.S. Cl. ................................................... 128/276
[58] Field of Search ............................ 128/275–278, 128/303.1, 24 A, 303 C; 32/33; 417/149

[56] References Cited

U.S. PATENT DOCUMENTS

| 2,727,678 | 12/1955 | Henderson | 128/276 UX |
| 3,565,076 | 2/1971 | Kadan | 128/278 |
| 3,589,363 | 6/1971 | Banko et al. | 128/276 |
| 3,812,855 | 5/1974 | Banko | 128/276 |

Primary Examiner—Robert W. Michell
Assistant Examiner—Henry S. Layton
Attorney, Agent, or Firm—Philip Sperber

[57] ABSTRACT

Apparatus is disclosed for aspiration of the operative site during open site surgery having automatic controls for responsively venting the aspiration system to atmosphere under certain conditions and for overriding the venting as desired comprising a continuously operating pump for providing suction, an aspiration line connected to the pump, a venting valve and, an aspiration valve in the aspiration line, a vacuum pressure responsive switch connected between the aspiration valve and the pump and a control system embodying activation switches and logic for controlling the operation of the valves.

6 Claims, 1 Drawing Figure

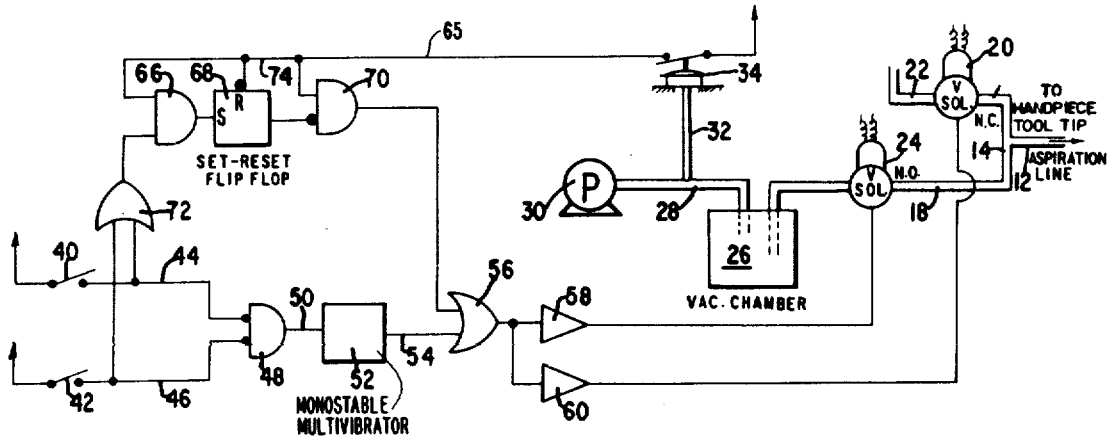

AUTOMATIC ASPIRATION APPARATUS

BACKGROUND OF THE INVENTION

This invention relates to a system for use in the irrigation and aspiration of open site surgery. More particularly the invention relates to an electronic control system embodying logic circuitry for the fail safe control of aspiration in combination with open site surgery particularly such surgery which employs ultrasonic or similar surgical tools for disintegrating tissue. One such surgical embodiment and procedure is disclosed in U.S. patent application Ser. No. 555,474 filed Mar. 5, 1975 for Neurosonic Aspirator and Method, wherein apparatus and method are shown for performing ultrasonic open site neurosurgical procedures. As part of such procedures the operative site is open to atmosphere in contrast to a generally accepted ultrasonic operative surgery for the removal of a cateract from the eye wherein the eye is the operative site and is essentially a closed operative site.

In the aforementioned systems, aspiration is an important feature of the operative procedure. By aspiration, what is conventionally meant is withdrawal of fluid from the operative site and more specifically withdrawal by suction of fluid. As such, aspiration is the result of suction applied through a small tubular opening and is so defined herein regardless of whether the suction is applied to an operative site such as the interior of the anterior capsule of the eye as in closed site surgery or from an open operative site where pressure gradients are not critical to the surrounding tissue or from a solution of sterile fluid for clearing the aspiration system.

In the prior art the aspiration system was controlled within certain critical pressure limits which were necessary for operations on the interior of the eye. However, for open site operative surgery, aspiration need not be controlled for purposes of obtaining a specific vacuum pressure and flow withdrawal rate, but aspiration is essential for keeping the view of the surgeon clear to assist him in effectively maintaining contact of the tissue and operative tool tip during ultrasonic vibration of the tool.

In this regard it is advantageous to automatically apply aspiration when the ultrasonic tool is activated. However aspiration is also generally useful without ultrasonic activation of the tool, as for instance to remove fluid and material from the operative site. (One would therefore suppose that aspiration may be continually operated. However it is necessary to release tissue which is not to be disintegrated with the ultrasonic tool). In prior art apparatus, separate switching modes were provided to separately allow aspiration alone or aspiration together with ultrasonic activation of the tool. In either case the aspiration mode is continually activated and deactivated. Such a mode of operation required the operator, realistically the surgeon, to select the desired mode and then operate the appropriate switch. Additionally since suction was obtained by using an electrical motor-driven pump to apply a vacuum, the motor is continually being turned on and off during operation. Such constant on-off switching of the motor subjects the electrical power switches to severe contact loading and the pump seals to continual uneven stress. Wear is particularly aggravated if the vacuum is retained (by tight seals) in the aspiration system resulting in added starting load on the pump motor.

Therefore it is an object of this invention to provide a fail-safe control system for operative surgery embodying aspiration;

It is still another object of this invention to provide an automatic control system for venting and applying aspiration in a surgical operating apparatus;

Yet another object of the present invention is to provide improved apparatus embodying simplified controls and improved reliability;

Still another object of this invention is to provide surgical aspiration apparatus having versatility, reliability and override capability;

Another object of the present invention is to provide an aspiration system having a self-cleaning capability.

Other objects and advantages of this invention will become apparent from the drawings and description of the preferred embodiment which follows.

SUMMARY OF THE INVENTION

We have invented an apparatus for controlling aspiration during surgery comprising, in combination, a continuous pump means for applying a vacuum, aspiration means communicatingly connected to the pump means at one end, a normally open aspiration valve mounted in the aspiration means, sensing means communicatingly connected to the aspiration means beyond the aspiration valve, a normally closed venting means communicatingly connected to the aspiration means before the aspiration valve for venting the aspiration means to about ambient pressure, and a first automatic logic means responsively connected to the sensing means for opening the venting means and closing the aspiration valve in response to excessive vacuum pressure buildup.

With the view of more fully describing the invention, the following description of the drawings and the preferred embodiment is given.

BRIEF DESCRIPTION OF THE DRAWINGS

The drawing is a block diagram of the aspiration system according to this invention.

DESCRIPTION OF THE PREFERRED EMBODIMENT

The (apparatus and) system of this invention is particularly applicable for use in combination with the apparatus shown in copending U.S. patent application 672,814 for ULTRASONIC ASPIRATOR of Robert Anderson, David Wuchinich and Alan Broadwin. In the aforesaid copending patent application, method and apparatus are disclosed for use in the surgical removal of tissue by utilization of an ultrasonically vibrating surgical tool to disintegrate the undesirable tissue while the operative site is supplied with sterile fluid (irrigation) and the resulting disintegrated tissues and various fluids are aspirated (withdrawn) from the operative site.

To enable the surgeon to control the operative procedure, various controls are employed. Specifically the surgeon should be able to control the application of irrigation, aspiration and ultrasonic activation of the apparatus and surgical tool as desired. Conceivably in open site surgery there is no criticality to the various possible combinations of irrigation, aspiration, and tool activation. However as is stressed in the aforesaid copending patent application direct observation of the tissue being subject to the surgical procedure is extremely important and of necessity it is therefore important to enable the surgeon to flush the operative site as desired and to remove disintegrated tissue and fluid therefrom. The apparatus provides for such irrigation and aspiration by utilization of controlled pumps to supply fluid to the site, (i.e. irrigation) and provide aspiration through a hollow tool tip to remove the tissue and fluid mixture from the site. This invention is directed to a system for controlling aspiration effectively and advantageously in such operative apparatus and procedures.

More specifically attention is now directed to the drawings showing an aspiration line 12 connected by suitable means to a hollow surgical tool tip (not shown) such as is shown by the aforementioned patent application. In turn the aspiration line 12 is connected at a T joint 14 to a vent line 16 and a vacuum line 18. Mounted in the vent line 16 is a normally closed solenoid vent valve 20 which is connected to a discharge line 22 open to atmospheric pressure and discharging to any suitable drain, or receptacle (not shown).

Aspiration line 18 has mounted therein a normally open electrically actuated solenoid aspiration valve 24 and the line continues from the valve 24 to a sealed collector chamber 26. Also connected to the collector chamber 26 is a vacuum pumpline 28 which is connected to the vacuum draw inlet of a continuously operating vacuum pump 30. (The vacuum pumps disclosed in the aforementioned prior art are not in continuous operation but operate in an on-off mode as desired. Clearly on-off operation of the vacuum pump motor is undesirable as opposed to continuous operation for reasons of vacuum buildup, motor reliability and load.) The present system according to our invention utilizes a continuous operation vacuum pump 30 and motor.

Connected to the pumpline 28 via a connector 32 is a vacuum pressure responsive electrical switch 34. The vacuum switch 34 is normally open and is adjusted to close at a preset vacuum pressure.

Therefore should the vacuum in the pumpline 28 and in the collector chamber build-up to a preselected high vacuum due either to a blockage in the aspirator line or to the closing of the aspirator solenoid valve, the vacuum switch will respond at the preset vacuum pressure and close. Basically the fluid system according to the present invention comprises the above described components. The remaining components of our invention comprise the logic and control circuit for the fluid system and are hereinafter described.

The applicable operator control switches are an 'ultrasonic' actuation switch 40 and an irrigation actuation switch 42. The vacuum pump is continuously operating and a vacuum is continuously applied to the chamber 26 and to the operative tool as long as the normally open (NO) aspiration valve 24 is open and the vent valve 20 closed.

During the open site operative procedure the hollow tool may become clogged as a result of tissue occlusion or importantly, tissue occlusion adjacent the aspirating tool tip, the tissue being held by the vacuum applied to the tool tip. It is important that the surgeon be able to release such tissue in contact with the tool as desired. For instance, if the surgeon is not interested in removing such tissue, the aspiration or applied vacuum must then be released. This is done by actuating the two solenoid valves opening the (NC) vent valve 20 and closing the (NO) aspiration valve 24. The surgeon accomplishes this by momentarily closing (actuating) either the ultrasonic switch 40 or the irrigation switch 42.

Each of the aforesaid activation switches 40 and 42 is connected via connectors 44 and 46 respectively to the input of an AND gate logic component 48. (By AND gate it is meant that logic element having two or more inputs in which the AND gate gives an output only if all inputs receive predetermined signals). The output 50 of the AND gate 48 is connected to the input of a monostable multivibrator 52. The output of the multivibrator 52 is in turn connected to one input 54 of an OR gate logic circuit 56. (Typically an OR gate is a logic component which produces an output (signal) whenever there are one or more inputs in a multi-channel input i.e., when any one or any combination of inputs occurs in time coincidence. Any gate may contain a number of inhibits in which there is no output under any condition of input if there is an inhibit or except signal).

The output of the OR gate 56 is directed to two 'drivers' specifically identified as the solenoid venting driver 60 and the solenoid aspiration driver 58. An excitation output from the OR gate 56 would activate the respective drivers 58 and 60 and open the solenoid vent valve 20 and close the aspiration valve 24, thereby immediately stopping all suction through the hollow aspirating tool tip and releasing any tissue held against the tool tip opening.

The vacuum buildup, generated by the continuously operating vacuum pump 30 against the closed aspiration valve 24, will act to close the pressure responsive vacuum switch 34 upon reaching the preset vacuum pressure.

The vacuum switch 34 is connected on its output side via output line 65 to one of the inputs each of a second AND gate 66, a set-reset flip-flop circuit 68 and a third AND gate 70. The two activation switches, specifically the ultrasonic switch 40 and the irrigation switch 42 are each also connected on their output side to a second OR gate 72. Activation of either or both of the aforesaid activation switches 40 or 42 will therefore produce an output signal from the second OR gate 72.

The output of the second OR gate 72 is connected to one of the inputs of the second AND gate 66, the other input being from the vacuum (pressure responsive) switch 34. The second AND gate's output is connected to the set input of the Set-Reset flip flop element 68 which will generate a steady output signal upon activation by the signal from the second AND gate 66. If the flip-flop 68 is producing the steady output signal to the third AND gate 70, the output of the flip-flop is cut off by the reset signal from the pressure switch 34 being cut off (opened) after activation. As shown by the input 74 to the third AND gate from the flip-flop circuit 68, absence of a signal from the flip-flop and presence of a signal from the pressure switch 34 to the third AND gate 70 will produce an output signal from the third AND gate to the OR gate 56, thereby activating the two valve drivers 60 & 58 to open and close the respective valves 20 and 24.

To recapitulate, the normal state of the system according to our invention is a continuous vacuum being supplied by the vacuum pump 30 through the collector chamber 26 and the open aspiration valve to the hollow tool tip for aspiration of the fluid and tissue picked up at the operative site. If the aspiration line 12 becomes occluded by tissue or the vacuum is allowed to build up by aspiration of a liquid such as blood or water rather than an air water, tissue mixture, the vacuum buildup will subsequently close the vacuum switch 34.

Closing the vacuum switch 34 will provide a signal at the inputs to the second AND gate 66, the reset to the flip-flop element 68 and one of the inputs to the third AND gate 70. Absence of an output from the flip-flop element to the third AND gate 7 will induce an output from the AND gate 70 to the first OR gate 56 triggering an output therefrom, thereby opening the vent valve and closing the aspiration line to atmosphere and releasing any occluded tissue and allowing the line to drain.

If the vacuum switch 34 is opened, the reset then cuts off the output of the flip-flop element 58, and the system is back to normal operating condition.

Normal operating condition can be achieved with the two activation switches 40 and 42 in closed position which would also prevent an output from the first AND gate 48 (which requires no signal from both of its inputs to produce an output).

Should both the switches be opened, then the first AND gate 48 produces an output to the monostable multivibrator 52. As previously described, the vibrator 52 is an element which produces an output signal for a limited preset time period, in this case about 2 second. The vibrator output will thereby activate the OR gate 56 output and power the drivers to open the vent valve 20 and close the aspiration valve 24 for this limited time. In short, if both activation switches are opened, the aspiration line would be cut off and the tool vented for a short period of time thereafter, after which it would automatically return to the aspiration condition. This limited period of time is not sufficient to allow buildup of the vacuum to trigger the vacuum switch, but it allows the surgeon to release tissue being held against the tool tip by suction.

In turn, activation of either the ultrasonic switch 40, the irrigation switch 42, or both, operates to produce an output from OR gate 72 to one of the inputs of the second AND gate 66. If the vacuum switch is also closed at this time, an output to the flip-flop element is generated which in turn generates a steady output to one of the inputs of the third AND gate 70. An output signal from the flip-flop 68 would act to prevent an output from the third AND gate and thereby deactivate the OR gate 56 signal to the drivers (thereby opening the aspiration valve and closing the vent valve). This provides an override to the vacuum switch, allowing suction to be applied as desired by the operator even though the vacuum switch is closed by the vacuum pressure buildup. This override mode is important in providing a means for aspiration liquids such as blood from the operative site or sterile solution. The override capability allows the surgeon to clean the site of blood as desired to improve vision. It also eliminates the need for other means to do so, while also enabling the surgeon to individually and rapidly do so with a unitary surgical tool. The override capability also allows the aspiration line to be purged quickly with a sterile solution. It is to be noted that normally the vacuum is applied to a mixture of air, liquid and tissue, and vacuum pressure would not build up to trigger the vacuum switch when such a fluid mixture is being aspirated. However, aspiration of a liquid stream as obtained by either blood or a sterile solution would normally build up vacuum pressure and trigger the vacuum switch and responsive elements if the override capability of the control system were not present.

Thus, the aforedescribed apparatus and control system provides a system which allows continuous operation of the vacuum pump; reduces the number of (activation) switches which must be directly operated by the surgeon, provides automatic safety features for releasing tissue from contact with the toolpiece; allows the tool to be cleaned or purged during operation; and increases the reliability of the system.

Having thus fully described the preferred embodiment of our invention and wishing to cover those variations and modifications which would be apparent to those skilled in the art without departing from either the spirit or scope thereof. We claim:

1. Apparatus for controlling aspiration from an operative site during surgery, said apparatus comprising:
   vacuum source means for providing a vacuum that is available continously;
   means connected to said source means for aspirating the operative site that includes (1) a normally open aspiration valve between the operative site and said source means, (2) vacuum pressure sensing means between said aspiration valve and said source means for sensing pressure in said aspiration means, (3) a normally closed venting means between the operative site and said aspiration valve for venting said aspiration means to about ambiant pressure, and (4) logic means responsively coupled to said sensing means for automatically opening said venting means and closing said aspiration valve, and activation control means coupled to said automatic logic means for overriding the automatic opening of said venting means and closing of said aspiration valve.

2. The apparatus according to claim 1 wherein said aspiration means further includes a sealed collection chamber between said aspiration valve and said source means.

3. The apparatus according to claim 1 wherein said sensing means comprises a vacuum pressure responsive switch means for providing an output signal in response to the vacuum pressure exceeding a preset limit in said aspiration means.

4. The apparatus according to claim 1 wherein said activation control means additionally includes further logic means coupled to said automatic logic means for momentarily opening said venting means and closing said aspiration valve.

5. The apparatus according to claim 4 wherein the overriding portion of said activation control means comprises:
   override activation means;
   a first AND gate coupled to said override activation means and said sensing means for producing an output signal in response to input signals from both said override activation means and said vacuum pressure sensing means, and
   a flip-flop element coupled to said first AND gate, said vacuum sensing means and a second AND gate, said flip-flop element producing a continuous signal to said second AND gate upon activation by the output from said first AND gate and responsively ending the continuous signal by the removal of a signal from said vacuum sensing means, said second AND gate being coupled to said vacuum sensing means and producing an output signal to open said venting means and close said aspiration valve when said output signal from said flip-flop element is absent and said output signal for said vacuum sensing means is present.

6. Apparatus according to claim 5 wherein said further logic means include a monostable multivibrator element coupled to said override activation means for producing a signal of preset duration to momentarily open said venting means and close said aspiration valve in the absence of a signal from said override activation means.

* * * * *